United States Patent
Tsai et al.

(10) Patent No.: US 7,355,095 B2
(45) Date of Patent: Apr. 8, 2008

(54) METHOD FOR PRODUCING HEART-SPECIFIC FLUORESCENCE OF NON-HUMAN EUKARYOTIC ANIMALS

(75) Inventors: Huai-Jen Tsai, Taipei (TW); Chiu-Ju Huang, Taipei (TW); Chung-Der Hsiao, Taipei (TW)

(73) Assignee: National Taiwan University, Taipei (TW)

( * ) Notice: Subject to any disclaimer, the term of this patent is extended or adjusted under 35 U.S.C. 154(b) by 0 days.

(21) Appl. No.: 11/017,814

(22) Filed: Dec. 22, 2004

(65) Prior Publication Data

US 2005/0273874 A1    Dec. 8, 2005

Related U.S. Application Data

(63) Continuation-in-part of application No. 10/079,528, filed on Feb. 22, 2002, now abandoned.

(51) Int. Cl.
*C12N 15/00* (2006.01)
*C07H 21/02* (2006.01)
*C07H 21/04* (2006.01)

(52) U.S. Cl. .................. 800/25; 800/20; 536/23.1

(58) Field of Classification Search ............... None
See application file for complete search history.

(56) References Cited

OTHER PUBLICATIONS

Meng, A et al. 1999, Blodd, 2:500-508.*
Huang, C-J et al, 2003, Developmental Dyanimcs, 228:30-40.*
Finley et al, Jul. 2001, Three-color imaging using fluorescent proteins in living zebrafish embryos, Biotechniques, 31:66-72.*
Franz, W-M et al. 1993, Heart-specifc targeting of firefly luciferase by the myosin light chain-2 promoter and developmental regulation in transgenic Circ. Res. 73:629-638.*
Motoike, T et al, 2000, Universal GFP reporter for the study of vascular development, Genesis, 28:75-81.*
Godwin, A.R., 1998, Detection of targeted GFP-Hox gene fusions during mouse embryogenesis, PNAS, 95:13042-13047.*
Tanaka, M et al. 2001, Establishment of medaka (*Oryzias latipes*) transgenic lines with the expressionof green, PNAS, 98:2544-2549.*
Ju, B. et al. Faithful expresion of green fluorescent protein (GFP) in transgenic zebrafish embryos under control zebrafish gene promotors, 1999, Development Genetics, vol. 25, pp. 158-167.*

* cited by examiner

*Primary Examiner*—Valarie Bertoglio
(74) *Attorney, Agent, or Firm*—WPAT, P.C.; Anthony King

(57) ABSTRACT

A method of expressing in vivo heart-specific fluorescence in transgenic line of zebrafish is developed, which provides a research model for studying heart-related gene functions and performing gene therapies in the future. The method comprises the following steps. Firstly, a plasmid is constructed. This plasmid construct includes the upstream regulatory region, the exon 1, the intron 1, and the exon 2 of cmlc2 gene, cDNA of GFP, wherein the cmlc2 gene and GFP cDNA form a cassette, and inverted terminal repeats from adeno-associated virus are flanked at both sides of this cassette. The plasmid construct is linearized and microinjected into one-celled zebrafish fertilized eggs. Lastly, the heart-specific fluorescent expressed zebrafish are selected and the germline-transmitting transgenic strain is generated.

11 Claims, 9 Drawing Sheets

```
TGTGACCAAA GCTTAAATCA GTTGTGTTAA ATAAGAGACA TTCAAAATAA    50
ATGTAAATGA GCTCTCCAAA TCAGCAGACT TAACATTCTT TAAATGATT    100
GATTCAATAG TGATACAAAT CAGGCATAGC AGTTGTAACT TTTGATAAAT   150
TACAGAAAAT GTCAAATACR GAGAACCGAT TCTTTTTTAT GACACATCCA   200
AGCACACATT TAACACAATC CAGGCAAACC CCGAATTTCA GAGTCACAAG   250
CACTGTTTGT ACAAGAGCTT TGCCTAAGGA CGCACAGTCT CTATGAGTCC   300
AGGTCGTTGG TTTCACTCTT ATTTTAAACA TGTGACATTT TTCCTGCCAT   350
CCTGTCTTAG GCTGCTGTTT GCTTCATTTC ATGTCACATT AATTTCCTCA   400
GTAGCACCTT TTACACACAC AGCCAATCTT TTCCAGAACA TTCAATTGCT   450
TTGAAGAGAT AATGTGTGAA CAAATCCATT TAGAAAAGGA AAATTAAGAA   500
TYTGTAAAAT CATCTGTAAA TTGTTGGCAT TCTTCTGTAT ATGAACATCA   550
CATCATTTAC AGGTAAAGGT CTGGTCATTA ATTATATGAC AATTTACTGG   600
TATTATTTTG TGAAGGGGC TATTTTCAAT GCATTCATCC ATCCTTTTCA   650
TCCCTCAAAT CTCTCATTCA CGTCCCCTC CCCATCTGCA CACTTTATCT   700
CATTTTCCAC CCTGCTGGAA TCTGAGCACT TGTGCAGTTA TCAGGGCTCC   750
TRTATTTAGG AGGCTCTGGG TGTCCATGTA GGGGACGAAC AGAAACACTG   800
CAGACCTTTA TAGAAGAACA AATGATAAGA GTCCTCATAC ATAAAGACTC   850
CATTAGAAAC GTCAGTGACC CAGGAGCCCA GACCAACAGC AAAGCAGACA   900
GTGAACATGG TGAGTAGACA AAGCTATACT TTTTGGTTT TGAATATAAT   950
ATTAATGTGA AAATAAAAAG GGTCTATATG AAGTTAAATG GTGTTTGTTT  1000
GTTGATATTA AATATTAGAA GCATCATTTT CTGCATTTGT ATGTTGTGAT  1050
TCTATCTTTT AATGAGTATT TTTACTTAGG TACTTTTTTC TGTACACTGT  1100
AAAACGCAAA AAAGTTAAGG TAACTCAAAT CATTTGAGAA AACCGATTGT  1150
AACAAGCCAT CTGAAGTTCA AAAACTAATC TAAATGAGTA CTGTGAACTT  1200
AATCTATTTG AGTAAAAGAA GCAATTTGAG CACAGTAAAA CCCAGTAAAT  1250
GAAGAGAACT CAACCAACTG AGTACTGTAA AACCCAATAA GTTGAGGCAG  1300
CTCACACCGT TAGAGGAAAC CGATTGCTAC AAACCATTTG AGTTAAAAAA  1350
AAGAATCTAT ATGAGTACTG TGAACTTACT CCATTTAAGT TGAAGTAATG  1400
AGGTAATTAA TTAACTCATT ACCCTCAACA CTAAGTTCAA AACTCTTTTC  1450
AAATGAGTAG AATTAATYTT CAGCCAATTT TGAGTTAACT ATACTCATTT  1500
CATTTGATAA AGTTGACTAT TGGGTTTTAC AGTGTATAAA TGCTATAAAT  1550
TGAGTTTCCA AATAATGCTT CTCTTTTTTT TTACTCACA GGCTAGTAAG   1600
AAAGCCGCGG CCAAGAGGGG GAAAACTGCT CAAAGAGGCT CTTCCAATGT  1650
CTTCTCCATG G                                          1700
```

FIG. 2

|  | Numbers | Percentage (%) |
|---|---|---|
| Total injected embryos | 86 | |
| Survival embryos (2dpf) | 51/86 | (60%) |
| EGFP-positive embryos | 30/51 | (60%) |
| Heart-specific expression | | |
| Uniform | 20/51 | (40%) |
| Mosaic | 5/51 | (10%) |
| Ectopic expression | 5/51 | (10%) |
| EGFP-negative embryos | 21/51 | (40%) |

FIG. 7

|  | Zebrafish (*Danio rerio*) | Medaka (*Oryzias latipes*) |
|---|---|---|
| Total embryos injected | 81 | 127 |
| Survival embryos | 69 (85%) | 114 (90%) |
| RFP expression | 29 (42%) | 50 (44%) |
| heart-specific | 22 (76%) | 37 (74%) |
| ectopic | 7 (24%) | 13 (26%) |

FIG. 8

|  | Zebrafish (*Danio rerio*) | Medaka (*Oryzias latipes*) |
| --- | --- | --- |
| Total embryos injected | 81 | 127 |
| Survival embryos | 69 (85%) | 114 (90%) |
| RFP expression | 29 (42%) | 50 (44%) |
| heart-specific | 22 (76%) | 37 (74%) |
| ectopic | 7 (24%) | 13 (26%) |

FIG. 9

SEQUENCE LISTING

<160> NUMBER OF SEQ ID NOS: 17

<210> SEQ ID NO 1
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
tgcgagtaag gatcctcacg caaggaattc cgaccagaca cc                           42

<210> SEQ ID NO 2
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
ctagggtgtc tggtcgc                                                      17

<210> SEQ ID NO 3
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
tgcgagtaag gatcctcacg ca                                                22

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
actccatccc ggttctgatc t                                                 21

<210> SEQ ID NO 5
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
ggagaagaca ttggaagagc ct                                                22

<210> SEQ ID NO 6
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
aacaactcga gtgtgaccaa agcttaaatc                                          30

<210> SEQ ID NO 7
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
ctcaaccatg gagaagacat tggaaga                                             27

<210> SEQ ID NO 8
<211> LENGTH: 1661
<212> TYPE: DNA
<213> ORGANISM: Artificial Sequence
<220> FEATURE:
<223> OTHER INFORMATION: Description of Artificial Sequence: Synthetic
      plasmid construct

<400> SEQUENCE: 8
tgtgaccaaa gcttaaatca gttgtgttaa ataagagaca ttcaaaataa atgtaaatga         60
gctctccaaa tcagcagact taacattctt taaaatgatt gattcaatag tgatacaaat        120
caggcatagc agttgtaact tttgataaat tacagaaaat gtcaaatacr gagaaccgat        180
tcttttttat gacacatcca agcacacatt taacacaatc caggcaaacc ccgaatttca        240
gagtcacaag cactgtttgt acaagagctt tgcctaagga cgcacagtct ctatgagtcc        300
aggtcgttgg tttcactctt attttaaaca tgtgacattt ttcctgccat cctgtcttag        360
gctgctgttt gcttcatttc atgtcacatt aatttcctca gtagcacctt ttacacacac        420
agccaatctt ttccagaaca ttcaattgct ttgaagagat aatgtgtgaa caaatccatt        480
tagaaaagga aaattaagaa tytgtaaaat catctgtaaa ttgttggcat tcttctgtat        540
atgaacatca catcatttac aggtaaaggt ctggtcatta attatatgac aatttactgg        600
tattattttg tgaaaggggc tattttcaat gcattcatcc atccttttca tccctcaaat        660
ctctcattca cgtccccctc cccatctgca cactttatct catttccac cctgctggaa         720 tctgagcact tgtgcagtta tcagggctcc trtatttagg aggctctggg tgtccatgta        780
ggggacgaac agaaacactg cagacccttta tagaagaaca aatgataaga gtcctcatac       840
ataaagactc cattagaaac gtcagtgacc caggagccca gaccaacagc aaagcagaca        900
gtgaacatgg tgagtagaca agctatact tttttggttt tgaatataat attaatgtga         960
aaataaaaag ggtctatatg aagttaaatg gtgtttgttt gttgatatta aatattagaa       1020
gcatcatttt ctgcatttgt atgttgtgat tctatctttt aatgagtatt tttacttagg       1080 tactttttc tgtacactgt aaaacgcaaa aaagttaagg taactcaaat catttgagaa        1140
aaccgattgt aacaagccat ctgaagttca aaaactaatc taaatgagta ctgtgaactt       1200
aatctatttg agtaaaagaa gcaatttgag cacagtaaaa cccagtaaat gaagagaact       1260
caaccaactg agtactgtaa aacccaataa gttgaggcag ctcacaccgt tagaggaaac       1320
cgattgctac aaaccatttg agttaaaaaa aagaatctat atgagtactg tgaacttact       1380
ccatttaagt tgaagtaatg aggtaattaa ttaactcatt accctcaaca ctaagttcaa       1440
aactcttttc aaatgagtag aattaatytt cagccaattt tgagttaact atactcattt       1500
catttgataa agttgactat tgggttttac agtgtataaa tgctataaat tgagtttcca       1560

-continued

```
aataatgctt ctctttttt tttactcaca ggctagtaag aaagccgcgg ccaagagggg    1620
gaaaactgct caaagaggct cttccaatgt cttctccatg g                       1661

<210> SEQ ID NO 9
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
ggccacgcgt cgactagtac tcccccccccc                                   30

<210> SEQ ID NO 10
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
ggtttgagat gatgctctac tcatagtc                                      28

<210> SEQ ID NO 11
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
tcatttggct agagaacatt gc                                            22

<210> SEQ ID NO 12
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
gccatcgtta caccttgata catat                                         25

<210> SEQ ID NO 13
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
cttccacttc ttcgttgtct gacat                                         25

<210> SEQ ID NO 14
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
```

```
acagctcctc gcccttgctc accat                                              25

<210> SEQ ID NO 15
<211> LENGTH: 1656
<212> TYPE: DNA
<213> ORGANISM: Artificial Sequence
<220> FEATURE:
<223> OTHER INFORMATION: Description of Artificial Sequence: Synthetic
      plasmid construct

<400> SEQUENCE: 15
gtgaccaaag cttaaatcag ttgtgttaaa taagagacat tcaaaataaa tgtaaatgag         60
ctctccaaat cagcagactt aacattcttt aaaatgattg attcaatagt gatacaaatc        120
aggcatagca gttgtaactt ttgataaatt acagaaaatg tcaaatacgg agaaccgatt        180
cttttttatg acacatccaa gcacacattt aacacaatcc aggcaaaccc cgaatttcag        240
agtcacaagc actgtttgta caagagcttt gcctaaggac gcacagtctc tatgagtcca        300
ggtcgttggt ttcactctta ttttaaacat gtgacatttt tcctgccatc ctgtcttagg        360
ctgctgtttg cttcatttca tgtcacatta atttcctcag tagcacccttt tacacacaca       420 gccaatcttt tccagaacat tcaattgctt tgaagagata atgtgtgaac aaatccattt        480
agaaaaggaa aattaagaat ttgtaaaatc atctgtaaat tgttggcatt cttctgtata        540
tgaacatcac atcatttaca ggtaaaggtc tggtcattaa ttatatgaca atttactggt        600
attattttgt gaaagggct attttcaatg cattcatcca tccttttcat ccctcaaatc         660
tctcattcac gtcccctcc ccatctgcac actttatctc attttccacc ctgctggaat         720
ctgagcactt gtgcagttat cagggctcct gtatttagga ggctctgggt gtccatgtag        780
gggacgaaca gaaacactgc agacctttat agaagaacaa atgataagag tcctcataca        840
taaagactcc attagaaacg tcagtgaccc aggagcccag accaacagca aagcagacag        900
tgaacatggt gagtagacaa agctatactt ttttggtttt gaatataata ttaatgtgaa        960
aataaaaagg gtctatatga agttaaatgg tgtttgtttg ttgatattaa atattagaag       1020
catcattttc tgcatttgta tgttgtgatt ctatctttta atgagtattt ttacttaggt       1080
acttttttct gtacactgta aaacgcaaaa aagttaaggt aactcaaatc atttgagaaa       1140
accgattgta acaagccatc tgaagttcaa aaactaatct aaatgagtac tgtgaactta       1200
atctatttga gtaaaagaag caatttgagc acagtaaaac ccagtaaatg aagagaactc       1260
aaccaactga gtactgtaaa acccaataag ttgaggcagc tcacaccgtt agaggaaacc       1320
gattgctaca aaccatttga gttaaaaaaa agaatctata tgagtactgt gaacttactc       1380
catttaagtt gaagtaatga ggtaattaat taactcatta ccctcaacac taagttcaaa       1440
actcttttca aatgagtaga attaatcttc agccaatttt gagttaacta tactcatttc       1500
atttgataaa gttgactatt gggttttaca gtgtataaat gctataaatt gagtttccaa       1560
ataatgcttc tcttttttttt ttactcacag gctagtaaga aagccgcggc caagaggggg       1620
aaaactgctc aaagaggctc ttccaatgtc ttctcc                                 1656

<210> SEQ ID NO 16
<211> LENGTH: 1676
<212> TYPE: DNA
<213> ORGANISM: Artificial Sequence
<220> FEATURE:
<223> OTHER INFORMATION: Description of Artificial Sequence: Synthetic
      plasmid construct
```

<400> SEQUENCE: 16

```
gtgaccaaag cttaaatcag ttgtgttaaa taagagacat tcaaaataaa tgtaaatgag      60
ctctccaaat cagcagactt aacattcttt aaaatgattg attcaatagt gatacaaatc     120
aggcatagca gttgtaactt ttgataaatt acagaaaatg tcaaatacgg agaaccgatt     180
cttttttatg acacatccaa gcacacattt aacacaatcc aggcaaaccc cgaatttcag     240
agtcacaagc actgtttgta caagagcttt gcctaaggac gcacagtctc tatgagtcca     300
ggtcgttggt ttcactctta ttttaaacat gtgacatttt tcctgccatc ctgtcttagg     360
ctgctgtttg cttcatttca tgtcacatta atttcctcag tagcaccttt tacacacaca     420
gccaatcttt tccagaacat tcaattgctt tgaagagata atgtgtgaac aaatccattt     480
agaaaaggaa aattaagaat ttgtaaaatc atctgtaaat tgttggcatt cttctgtata     540
tgaacatcac atcatttaca ggtaaaggtc tggtcattaa ttatatgaca atttactggt     600
attattttgt gaaaggggct attttcaatg cattcatcca tccttttcat ccctcaaatg     660
gccccagcca ctgtctcttt aaccttgaag gcattttggg gtctcacgtg tccacccagg     720
cgggtgtcgg actttgaacg gctcttaact tcagaagaac ggcatgggggt ggggggggctt     780
aggtggcctc tgcctcacct acaactgcca aaagtggtca tggggttatt tttaacccca     840
gggaagaggt atttattgtt ccacagcagg ggccggccag caggctcctt gaattcttca     900
gaggcagcag ccagcctcag acaccatggt gagtagacaa agctatactt ttttggtttt     960
gaatataata ttaatgtgaa ataaaaaagg gtctatatga agttaaatgg tgtttgtttg    1020
ttgatattaa atattagaag catcattttc tgcatttgta tgttgtgatt ctatctttta    1080
atgagtattt ttacttaggt actttttttct gtacactgta aaacgcaaaa aagttaaggt    1140
aactcaaatc atttgagaaa accgattgta acaagccatc tgaagttcaa aaactaatct    1200
aaatgagtac tgtgaactta atctatttga gtaaaagaag caatttgagc acagtaaaac    1260
ccagtaaatg aagagaactc aaccaactga gtactgtaaa acccaataag ttgaggcagc    1320
tcacaccgtt agaggaaacc gattgctaca aaccatttga gttaaaaaaa agaatctata    1380
tgagtactgt gaacttactc catttaagtt gaagtaatga ggtaattaat taactcatta    1440
ccctcaacac taagttcaaa actcttttca aatgagtaga attaatcttc agccaatttt    1500
gagttaacta tactcatttc atttgataaa gttgactatt gggttttaca gtgtataaat    1560
gctataaatt gagtttccaa ataatgcttc tcttttttttt ttactcacag gctagtaaga    1620
aagccgcggc caagaggggg aaaactgctc aagaggctc ttccaatgtc ttctcc          1676
```

<210> SEQ ID NO 17
<211> LENGTH: 1678
<212> TYPE: DNA
<213> ORGANISM: Artificial Sequence
<220> FEATURE:
<223> OTHER INFORMATION: Description of Artificial Sequence: Synthetic
    plasmid construct

<400> SEQUENCE: 17

```
gtgaccaaag cttaaatcag ttgtgttaaa taagagacat tcaaaataaa tgtaaatgag      60
ctctccaaat cagcagactt aacattcttt aaaatgattg attcaatagt gatacaaatc     120
aggcatagca gttgtaactt ttgataaatt acagaaaatg tcaaatacgg agaaccgatt     180
cttttttatg acacatccaa gcacacattt aacacaatcc aggcaaaccc cgaatttcag     240
agtcacaagc actgtttgta caagagcttt gcctaaggac gcacagtctc tatgagtcca     300
```

```
ggtcgttggt ttcactctta tttttaaacat gtgacatttt tcctgccatc ctgtcttagg    360
ctgctgtttg cttcatttca tgtcacatta atttcctcag tagcaccttt tacacacaca    420
gccaatcttt tccagaacat tcaattgctt tgaagagata atgtgtgaac aaatccattt    480
agaaaaggaa aattaagaat ttgtaaaatc atctgtaaat tgttggcatt cttctgtata    540
tgaacatcac atcatttaca ggtaaaggtc tggtcattaa ttatatgaca atttactggt    600
attattttgt gaaagggggct atttttcaatg cattcatcca tcctttttcat ccctcaaata   660 gggcctcctg gtgtgctgct aaccttgaaa gcctctgtgt ctcgcatgtc acgtcggcca    720
gtgacaacag caagcttact gcagattaga ggaggagaaa gtcagagaca agagggtcgg    780
gggtggctgg tttacctatt acagccaaaa gtggacatgg ggttatttttt agcctggaat    840 ggggtgtatt tattgtttca gcccagggag gcagagggac tgcctctgag attcctcctg    900
cagcaccacc agcacctctg cgaagacatg gtgagtagac aaagctatac ttttttggtt    960
ttgaatataa tattaatgtg aaaataaaaa gggtctatat gaagttaaat ggtgtttgtt   1020
tgttgatatt aaatattaga agcatcattt tctgcatttg tatgttgtga ttctatcttt   1080
taatgagtat ttttacttag gtactttttt ctgtacactg taaaacgcaa aaaagttaag   1140
gtaactcaaa tcatttgaga aaaccgattg taacaagcca tctgaagttc aaaaactaat   1200
ctaaatgagt actgtgaact taatctattt gagtaaaaga agcaatttga gcacagtaaa   1260
acccagtaaa tgaagagaac tcaaccaact gagtactgta aaacccaata agttgaggca   1320
gctcacaccg ttagaggaaa ccgattgcta caaaccatt gagttaaaaa aaagaatcta   1380
tatgagtact gtgaacttac tccatttaag ttgaagtaat gaggtaatta attaactcat   1440
taccctcaac actaagttca aaactctttt caaatgagta gaattaatct tcagccaatt   1500
ttgagttaac tatactcatt tcatttgata aagttgacta ttgggtttta cagtgtataa   1560
atgctataaa ttgagtttcc aaataatgct tctctttttt tttactcac aggctagtaa   1620 gaaagccgcg gccaagaggg ggaaaactgc tcaaagaggc tcttccaatg tcttctcc    1678
```

METHOD FOR PRODUCING HEART-SPECIFIC FLUORESCENCE OF NON-HUMAN EUKARYOTIC ANIMALS

FIELD OF THE INVENTION

This application is a Continuation in Part of U.S. Ser. No. 10/079,528 filed Feb. 22, 2002 which is now abandoned. The present invention relates to a method of generating a transgenic line of fish labeled with heart-specific fluorescence in vivo to serve as a model system for heart-related researches.

BACKGROUND OF THE INVENTION

Heart disease is one of the most common causes of death in the world and the most troublesome symptoms. Accordingly, a large number of researchers are currently searching for a simple animal model system to assist in finding either a cure for heart-related diseases or a novel gene capable of regulating heart development.

Franz et al. (1991, Eur. Heart Jour., Vol. 12, page 210) taught producing a transgenic mice comprising a transgene encoding the firefly luciferase gene under the control of the rat cmlc2 promoter wherein the mice specifically express luciferase in the heart. In brief, two DNA constructs containing a luciferase reporter gene (LRG) under the control of the rat cardiac myosin-light-chain-2 (MLC-2) prmoter/enhancer (P/E) were injected into fertilized mouse oocytes. The first construct, designated (2.1 kb/Luc), spanned 20.1 kb of the 5' noncoding region of MLC-2. The second construct designated (260 bp/Luc) contained the minimal required sequence for cardiac myocyte specific expression as demonstrated in vitro. Hearts of transgenic mice expressed up to 100 pg LRG per mg of extracted protein. Neither in skeletal muscle, uterus or other organs LRG activity was detected. Hence, Franz et al. concluded that rat cardiac MLC-2 P/E is exclusively active in the myocardium, providing the possibility of gene targeting to the heart of transgenic animals.

It is noted that the in vivo model system of the transgenic mice illustrated above has some drawbacks. The mouse embryos developed from fertilized oocytes with two DNA constructs injected thereinto cannot allow an investigator to observe expression of the transgene directly. In other words, because embryos of mice are not transparent, the investigator cannot observe gene expression from early developmental stage, e.g. embryonic stage, to late developmental stage, e.g. mature stage, of mice. Under the situation, sacrifices of valuable animals, such as mice, are unavoidable.

Fish are the simplest vertebrates with heart organs. Among these fish, those which develop from transparent embryos, such as zebrafish (*Danio rerio*) and medaka (*Oryzias latipes*), have become an alternative model system for heart-related researches. The tendency derives from the following reasons: 1) organ developments can be easily observed since embryos of the fish are transparent. In this case, physiological and pathological variations, which may result from environmental pollutants, therapeutic drugs or other factors, during organogenesis can be facilely investigated as well. 2) experimental and investigative duration is greatly shortened due to rapid proceeding of embryogenesis. For example, the heart of the zebrafish starts to beat at about 24 hours postfertilization (hpf) and well develops within 48 hpf. 3) sacrifices of fish are unnecessary because contractibility of the heart can be directly observed from their appearances; and 4) large-scale screenings for mutant species are allowed.

Although using fish described above to serve as model systems possess many advantages, such model systems labeled with heart-specific fluorescence in vivo have not been established yet.

SUMMARY OF THE INVENTION

The first object of the present invention is to provide a method of expressing in vivo heart-specific fluorescence, serving as a research model, in non-human eukaryotic animals to trace the cell-fate of heart cells.

The second object of the present invention is to provide a method of expressing in vivo fluorescence, serving as a research model, in non-human eukaryotic animals to search for new heart-specific genes.

The third object of the present invention is to provide a method of expressing in vivo heart-specific fluorescence, serving as a research model, in non-human eukaryotic animals to serve as biological indices of environmental pollutants.

The fourth object of the present invention is to provide a method of expressing in vivo heart-specific fluorescence, serving as a research model, in non-human eukaryotic animals to study the influences of new drugs applied to heart development and therapy.

A method of expressing in vivo heart-specific fluorescence in transgenic line of zebrafish is developed, which provides a research model for studying heart-related gene functions and performing drug and gene therapies in the future. The method comprises the following step. A fluorescent protein gene is integrated into the genome of a non-human eukaryotic animal. In a preferred embodiment, a gene encoding green fluorescent protein (GFP) is transferred into the genome of a zebrafish. The transgenic process comprises the following steps. First, the genomic DNA of zebrafish larvae are extracted and cut with a restriction enzyme at 37° C. Then, the DNA fragments are ligated with adaptors, Pad1 and PR-SpeI. After ligation, polymerase chain reaction (PCR) is performed twice to amplify the target DNA segment. The amplified segment is subjected to gene sequencing steps for determining the nucleotide sequence, which is the 5' region of zebrafish cardiac myosin light chain 2 (cmlc2) gene. Subsequently, a plasmid is constructed. This plasmid includes the upstream regulatory region, the exon 1, the intron 1, and the exon 2 of cmlc2 gene, cDNA of GFP, wherein the cmlc2 gene fused with GFP cDNA form a cassette, and inverted terminal repeats from adeno-associated virus are flanked at both sides of this cassette. The plasmid construct is linearized with NotI digestion and subsequently microinjected into one-celled zebrafish fertilized eggs. Lastly, the heart-specific fluorescence expressed in embryos is screened under a fluorescence microscope. These putative founders mate with wild-type strains. A germ-line transmission of zebrafish possessing heart-specific fluorescence is developed.

BRIEF DESCRIPTION OF THE DRAWINGS

The foregoing aspects and many of the attendant advantages of this invention will become more readily appreciated and understood by referencing the following detailed description in conjunction with the accompanying drawings, wherein:

FIG. 2 is a structural view of a linearized plasmid construct (SEQ ID NO: 8) illustrating the segment compositions of the construct for gene transferring in accordance with the present invention.

FIG. 7 shows results of microinjecting pICMLE into embryos of medaka in accordance with the present invention FIG. 8 shows results of microinjecting pICMLE into embryos of zebrafish and medaka in accordance with the present invention.

FIG. 9 shows results of microinjecting pICMLR into embryos of zebrafish and medaka in accordance with the present invention.

DETAILED DESCRIPTION OF THE PREFERRED EMBODIMENT

Figure 1:
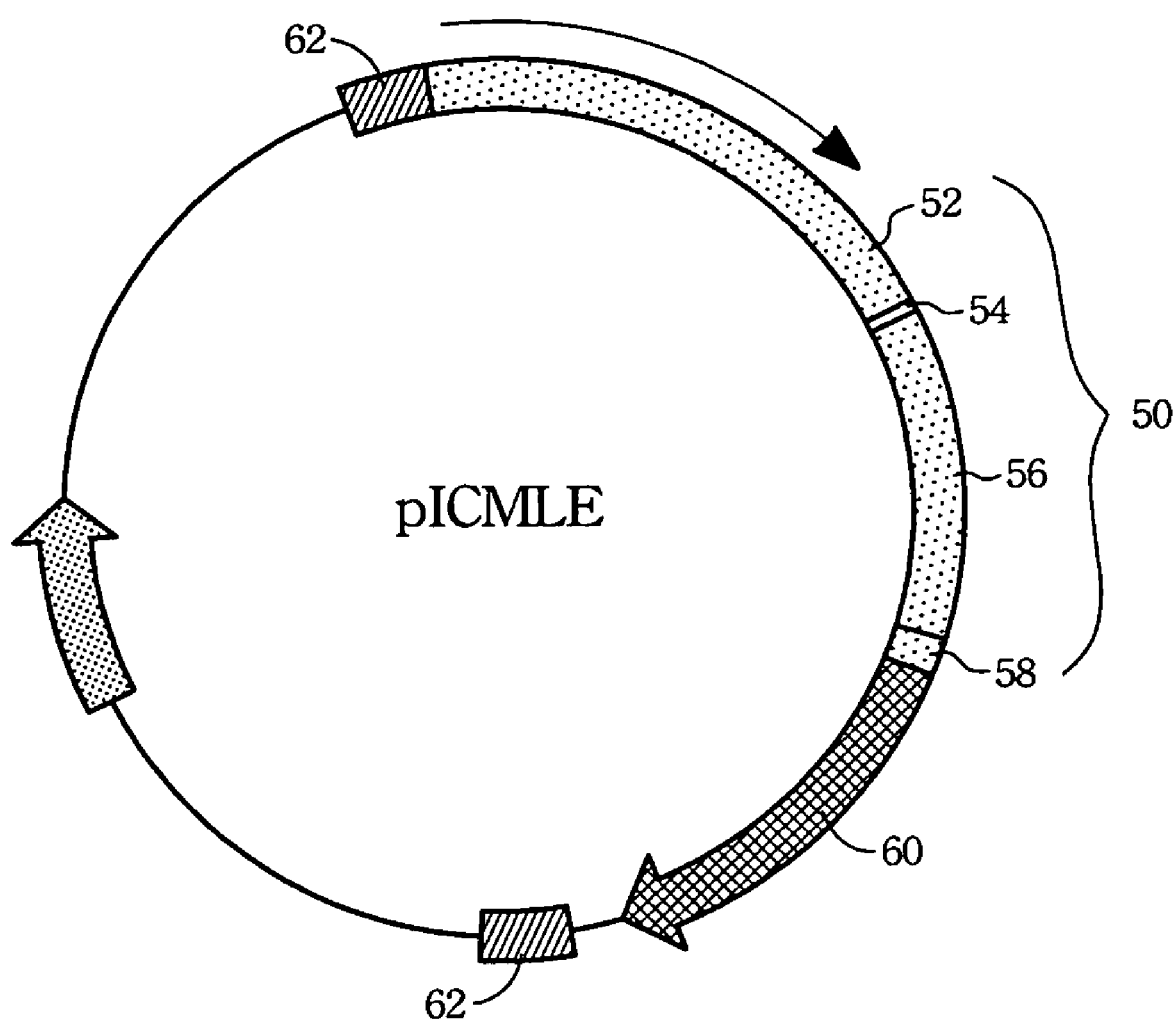
FIG. 1 is a structural view of a plasmid construct, pIC-MLE, illustrating the composition of the construct in accordance with the present invention.

A method is disclosed hereinafter to provide a method of generating a transgenic line of fish labeled with heart-specific fluorescence in vivo to serve as a model system for heart-related researches. The model system is useful in tracing the developmental fates of heart cells, finding new heart-specific genes and functions, establishing biological indices of environmental pollutants and studying the efficacy of therapeutic drugs. Below, embodiments will be described in detail according to drawings.

EXAMPLES

Example 1

1.01 Zebrafish Breeding

A zebrafish AB strain was cultured and maintained according to procedures described by Westerfield (1995). Embryonic stages were recorded as hpf and days postfertilization (dpf) following Kimmel et al. (1995).

1.02 Genomic DNA Extraction and Restriction Enzyme Digestion

Genomic DNA was extracted from zebrafish larvae at 48 hpf. One microgram of the extracted DNA was then added into 50 µl restriction enzyme buffer (50 mM NaCl, 10 mM Tris-HCl, 10 mM $MgCl_2$, 1 mM DTT, pH 7.9) and cut with SpeI restriction enzyme at 37° C. The DNA sample was purified by ethanol precipitation.

1.03 Adaptor Ligation

One microgram of SpeI-cut DNA fragment and 100 pmol each of Pad1 (5'-TGCGAGTAAGGATCCTCACGCAAG-GAATTCCGACCAGACACC-3') (SEQ ID NO: 1) and PR-SpeI (5'-CTAGGGTGTCTGGTCGC-3') (SEQ ID NO: 2) adaptors were added to a final volume of 20 µl of ligation buffer. The mixture was preheated in a GeneAmp PCR system at 70° C. for 20 minutes and then slowly cooled down to 4° C. (this took about 3 hours). After cooling, 6 units of AvrII restriction enzyme and 3 units of T4 DNA ligase (Promega) were added and reacted at 4° C. for 16 hours. Unligated adaptors were removed with Microcon-100 (Amicon) and the final volume of the sample was 50 µl. One µl DNA sample was used for the following PCR.

1.04 Polymerase Chain Reaction (PCR) and its Product

Target DNA was amplified by performing PCR twice. The first PCR was conducted in 20 µl of solution containing 20 ng of DNA (ligated with adaptors serving as a DNA template), 1 pmol of P1 primer (5'-TGCGAGTAAGGATCCT-CACGCA-3') (SEQ ID NO: 3), 4 pmol of CML1 primer (5'-ACTCCATCCCGGTTCTGATCT-3') (SEQ ID NO: 4), 200 pmol of each dNTP, and 1 unit of VioTaq DNA polymerase (Viogene). Firstly, solution was heated at 94° C. for 1 minute to denature the DNA. Subsequently, the PCR was performed for 35 cycles. Each cycle was conducted at 94° C. for 30 seconds and then at 68° C. for 6 minutes. Finally, this solution was treated at 68° C. for 8 minutes.

The second PCR was conducted by using 1 µl of the first PCR product, 4 pmol of P1 primer, 4 pmol of CML2 primer (5'-GGAGAAGACATTGGAAGAGCCT-3') (SEQ ID NO: 5), and 1 unit of ExTaq (Takara). Secondary PCR products were identified using agarose gel electrophoresis.

1.05 DNA Sequencing

The PCR product (1.6 kb) was purified from the agarose gel and inserted into pGEM-T vector for DNA sequencing. This PCR product was confirmed as the upstream regulatory region, exon 1, intron 1, and exon 2 of the zebrafish cmlc2 gene.

1.06 Plasmid Construct

Primers, CML4-XhoI (5'-AACAACTCGAGTGTGAC-CAAAGCTTAAA-TC-3') (SEQ ID NO: 6) and CML2-NcoI (5'-CTCAACCATGGAGAAGACATTGGAAGA-3') (SEQ ID NO: 7) were designed using the sequences of the 1.6-kb PCR-product described in the preceding section. The uncut chromosomal DNA was served as a DNA template. The PCR was conducted in 50 µl of solution containing 100 ng DNA template, 10 pmol of each primer (CML4-XhoI and CML2-NcoI), 200 pmol of each dNTP, and 1 unit of ExTaq. Firstly, sample was heated at 94° C. for 1 minute to denature the DNA. Subsequently, the PCR was performed for 30 cycles. Each cycle was performed at 94° C. for 30 seconds, and then at 68° C. for 3 minutes. Lastly, the sample was treated at 68° C. for 8 minutes.

The final PCR product was cut with 20 units of the XhoI and NcoI in restriction enzyme buffer (50 mM NaCl, 10 mM Tris-HCl, 10 mM $MgCl_2$, 1 mM DTT, pH 7.9) at 37° C. for 20 hours. After that, the product was purified from the agarose gel and ligated into a plasmid pEGFP-ITR already cut by XhoI and NcoI. The resulting plasmid construct encompassing a cmlc2 gene of the zebrafish had 5937 bp and was designated as pICMLE. Referring to FIG. 1, the nucleotide sequence of the cmlc2 gene 50 includes a 870-bp segment of the 5' upstream regulatory region 52 (454-1323), a 39-bp segment of the exon 1 54 (1324-1362), a 682-bp segment of the intron 1 56 (1363-2044) and a 69-bp segment of the exon 2 58 (2045-2110). This 1.6-kb segment (FIG. 2) was then fused with GFP cDNA 60 (CLONETECH) to form a cassette. The cassette was flanked on its both sides by 145-bp inverted terminal repeats 62 (260-1323 and 3128-3264, respectively) which are derived from an adeno-associated virus (AAV-ITR). Between the inverted terminal repeat 62 (3128) and the stop codon of the GFP cDNA 60 (2830) included a fragment containing SV40 poly-A signal sequence 61 (2931-2983). As shown in FIG. 1, the pICMLE further comprised f1 single-strand DNA origin 64 (3499-

3953), ampicillin resistance gene 66 (start codon 4085-4087; stop codon 4943-4945) and Col Elorigin of replication 68 (5093-5736).

According to a primer extension essay, the transcription initiation site (+1) of the zebrafish cmlc2 was 36 bp upstream of the start codon. Based on the results of analysis of the −210/39 region conducted by using the TRSEARCH (version 1.3) program, we propose that several putative cis-elements might be linked to a family of DNA binding proteins such as GATA, Cdx, MZF, CREB, and NKx either on the coding strand or on the noncoding strand.

1.07 Rapid Amplification of cDNA Ends and Primer Extension

Basically, the 5'-rapid amplification of cDNA ends (RACE) procedure followed the method described by Huang et al. (*Mol Reprod Dev* 54: 223-231), except that a forward primer (5'-GGCCACGCGTCGACTAGTACTC-CCCCCCCC-3') and a reverse primer (5'-GGTTTGAGAT-GATGCTCTACTCATAGTC-3') were used along with an annealing temperature of 58° C.

After performing the 5'-RACE and combining it with part of the cDNA taken from AF114428 (Yelon et al., *Dev Biol* 214: 23-37), a complete cDNA of the zebrafish cmlc2 was obtained. The cDNA encodes a putative polypeptide with 172 amino acid residues (GenBank accession no. AF425743). The deduced amino acid sequence of the zebrafish cardiac MLC-2 polypeptide shared 39, 46, 74, and 60% identity with the sequences of *D. melanogaster* (AAL25408), *C. elegans* (NP510828), mouse MLC-2a (NP075017), and mouse MLC-2v (AAB37470), respectively.

1.08 Gene Transfer and Fluorescent Signal Observations

Figure 3:
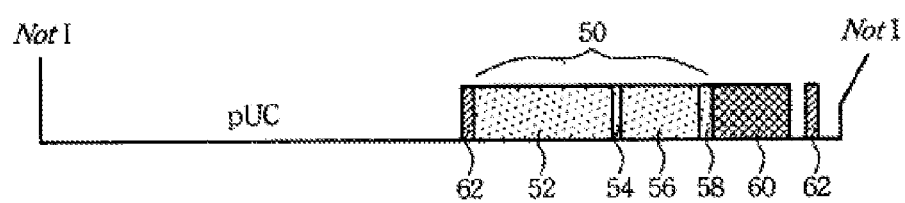
FIG. 3 shows the nucleotide sequence of the partial zebrafish cmlc2 gene.

Fertilized eggs were collected with a plastic capillary and placed in a holder. A glass needle with 10 μm opening was filled with the NotI-cut plasmid pICMLE (FIG. 3) solution and mounted with mineral oil. 2-4 nl of the DNA sample was then microinjected into the one-cell fertilized eggs of zebrafish. That is, the transgene comprising the regulatory region of the cmlc2 gene of the zebrafish and the gene fragment encoding the GFP was injected into the genome in the transparent embryo of zebrafish.

The injected fertilized eggs were incubated at 28° C. in dishes containing low concentration of methylene blue solution. Heart development and GFP expression in embryos were observed by using a fluorescence microscope.

After injecting the plasmid construct into the fertilized eggs for three days, a 50 to 70% survival rate of the transferred zebrafish embryos was obtained. Transient transgenic assay showed that 45-50% of the surviving embryos displayed cardiac tissue-specific GFP expression. Five days later, the heart-specific fluorescent zebrafish were moved to an aquarium. Sexual maturation achieved after 12 weeks.

1.09 Germ-line Transmission of cmlc2::GFP Transgenic Zebrafish

To generate germ-line transmitting transgenic zebrafish, the linearized pICMLE was injected into one-cell fertilized eggs of the zebrafish eggs. Approximately 50% of injected embryos expressed GFP in heart were raised to adulthood. Pairs of male and female founders were initially mated to screen for transgenic zebrafish. If GFP expression was found in some of the resulting embryos, the founders were separated and allowed to mate with wild strains to identify the putative germline transmitting parent. One pair each of transgenic and wild zebrafish were kept in a 22×14×13 cm$^3$ tank. A minimum of 200 embryos were examined per cross.

Figure 4:
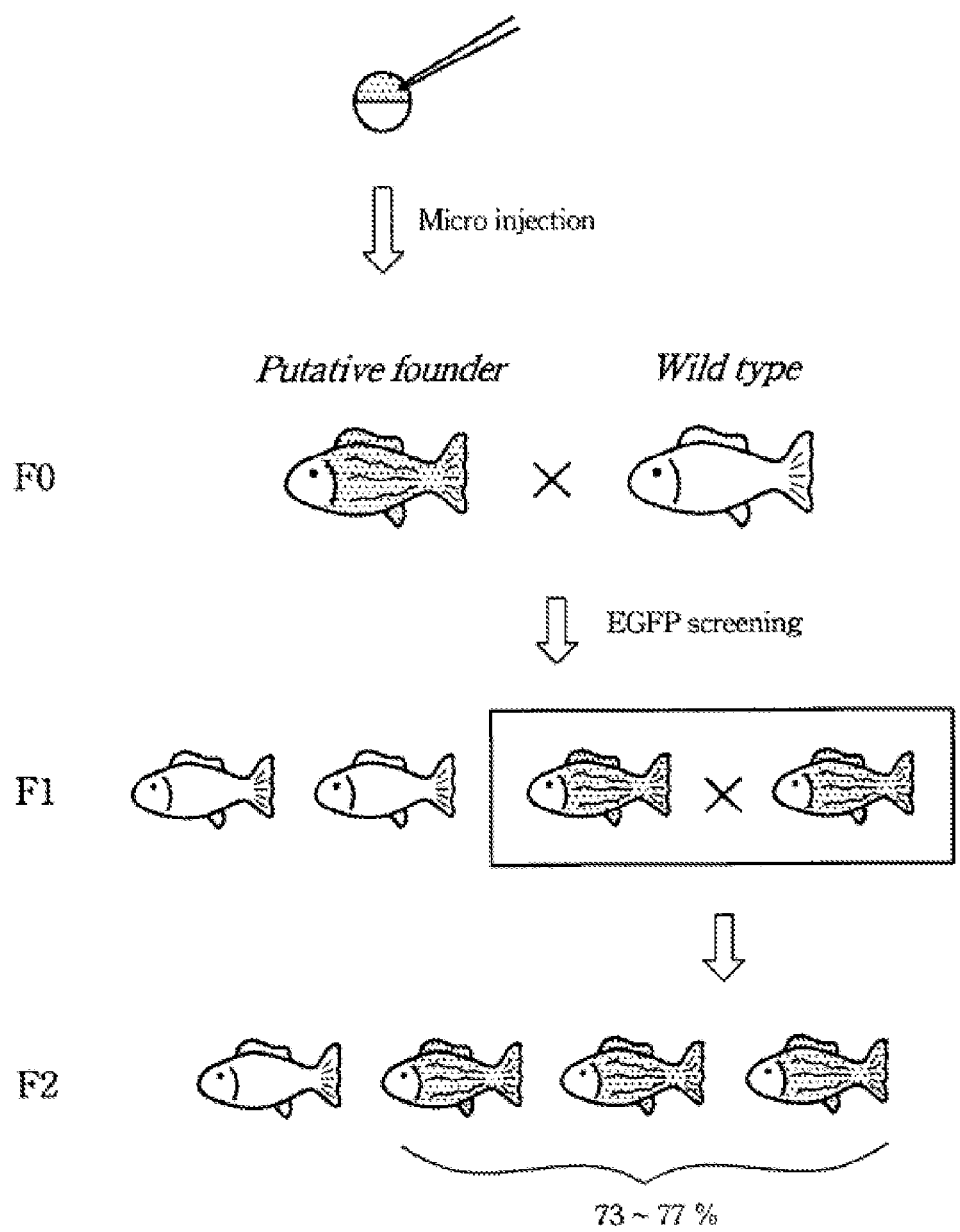
FIG. 4 shows the germ-line transmission of green-heart transgenic F2 derived from inter-crossing between two fluorescent F1 progeny in accordance with the present invention.

Among 324 founders, 37 individuals (11.4%) produced offspring that expressed GFP, including 34 showing heart-specific fluorescence. The transgen transmission rates from F1 to F2 were approximately 50%. Transmission rates resulting from inter-crossing of two F1 zebrafish showed that fluorescence ranged between 73 and 77% (FIG. 4). These data fit well with standard Mendelian inheritance ratios, indicating that the transgene was integrated into a single chromosomal locus. The heart-specific fluorescence was observed in the zebrafish throughout their life spans.

The GFP-labeled hearts of F3 homozygotic transgenic zebrafish were observed at high resolution during the embryonic stage. Successive atrium and ventricle contractions were easily observed on both sides of individual fish. The atrium and the ventricle were highly organized into a compact structure, which could be easily observed at 7 dpf.

1.10 Whole-mount in Situ hybridization

To analyze the fidelity of transgenic GFP expression driven by the regulatory region of cmlc2 that was cloned, the endogenous cmlc2 expression after whole-mount in situ hybridization in developing embryos was studied.

Whole-mount in situ hybridization with digoxigenin (DIG)-labeled riboprobes was performed according to the protocol described by Jowett (*Methods* 23: 345-358). PCR products amplified from pGEM-T containing full lengths of cmlc2 cDNA with T7 primers were used to synthesize riboprobes using a DIG RNA Labeling Kit (Roche), followed by in vitro transcription reaction with T7 RNA polymerase. Whole-mount embryos were cleaned in 100% methanol, placed in 100% glycerol, and evaluated with a differential interference contrast microscope (DMR, Leica) equipped with a COOLPIX 990 color digital camera (Nikon).

Results showed that the zebrafish cmlc2 was activated in the bilateral heart field around 16 hpf and that cardiac cells expressing cmlc2 were fused in a single heart tube and elongated by convergent extension by 24 hpf. It is noticed that cmlc2 transcripts were unevenly expressed in the atrium and ventricle by 48 hpf. The intensity of expression in the ventricle was much higher than that in the atrium.

1.11 Histology Section and GFP Observations

Adult zebrafish (3 months) of transgenic line (A34) were fixed with 4% paraformaldehyde in 1× phosphate buffered saline for 16 hr. Hearts were incubated directly into OCT without washing, and were serially cryosectioned with a thickness of 10 μm (MICROM HM5000). The sections were observed and photographed under a fluorescence microscope and a Nomarski microscope.

1.12 Injections of Morpholino Oligonucleotides

For targeted knockdown of the nkx2.5 and gata4 genes, morpholino antisense oligonucleotides of nkx2.5-MO (TCATTTGGCTAGAGAACATTGC) and gata-4-MO (GC-CATCGTTACACCT TGATACATAT) (SEQ ID NO:11) were synthesized (GeneTools, LLC). Each MO was injected at concentrations of 2.3, 4.6, 9.2, and 11.5 ng per embryo derived from the cmlc2:GFP transgenic line. nkx2.5-MO combined with gata-4-MO at a concentration of 4.6 ng was also injected. As for the control groups, we injected the following: (1) cTnT-MO (CTTCCACTTCTTCGTTGTCT-GACAT) (SEQ ID NO: 13) into embryos, because Sehnert et al. (J Cell Biol 157:873-882) reported that cTnT-MO produced a silent heart in zebrafish; and (2) EGFP-MO (ACAGCTCCTCGCCCTTGCTCACCAT) (SEQ ID NO: 14) into embryos as a positive control. Approximately 20-30 surviving embryos of each group were used to measure the beating rate of heart and to observe the intensity of GFP fluorescent signal.

1.13 Endogenous cmlc2 Expression and Transgenic GFP Expression Driven by the Cloned Regulatory Region of cmlc2

To analyze the fidelity of transgenic GFP expression driven by the regulatory region of cmlc2 that was cloned, the endogenous cm/c2 expression after whole-mount in situ hybridization in developing embryos was studied. Results showed that the zebrafish cmlc2 was activated in the bilateral heart field around 16 hpf and that cardiac cells expressing cmlc2 were fused in a single heart tube and elongated by convergent extension by 24 hpf. It was also noticed that cmlc2 transcripts were unevenly expressed in the atrium and ventricle by 48 hpf. The intensity of expression in the ventricle was much higher than that in the atrium.

F2 progeny were inter-crossed to produce a homozygotic F3 generation. The time of initial GFP detection in the transgenic lines varied: in 35 of 37 lines, GFP was activated by 20 hpf, approximately 4 hr after the detection of the endogenous cmlc2 transcripts. In two lines (A34 and A130), GFP was visible at approximately 16 hpf, which was exactly the stage at which the endogenous cmlc2 was detected by means of whole-mount in situ hybridization. At 24 hpf (after zebrafish hearts begin to beat), robust expression of GFP was noted in fish heart tubes. Although GFP expression was uniform in both the atrium and ventricle at 48 hpf, the GFP intensity in a given chamber was dependent on which chamber was contracting when the picture was taken. The cardiac-specific GFP driven by the cmlc2 promoter appeared throughout the life spans of all transgenic individuals.

1.14 GFP Transgene Was Expressed in All Myocardial Cells

The GFP expression driven by the cmlc2 promoter in the embryos of a transgenic line (A34) was examined. When hearts were cryosectioned, the GFP signals were intensively observed in the ventricular trabeculae, compact layer, and arterial pectinate muscle. No green fluorescence was seen in the bulbus arteriosus, trabecular folds, or leaflet valves of the atrioventricular and bulboventricular. Furthermore, by using an Axioplan microscoping with Nomarski optics, it was found that green fluorescent signals appeared specifically in the myocardium cells of the atrium, ventricle, and atrioventricular boundary. The epicardium, endocardium, and cushion all showed no green fluorescence. Green fluorescence could be traced in the trabeculae of 79-hpf embryos when the myocardium started to trabeculate. This signal became more prominent in the trabeculae of 5-dpf embryos, in which the ventricles showed extensive trabeculation. No morphologic defects of hearts were observed in transgenic zebrafish lines. The transgene had been stably transmitted to the F4 generation.

1.15 Promoter Analysis of Zebrafish cmlc2

Figure 5:
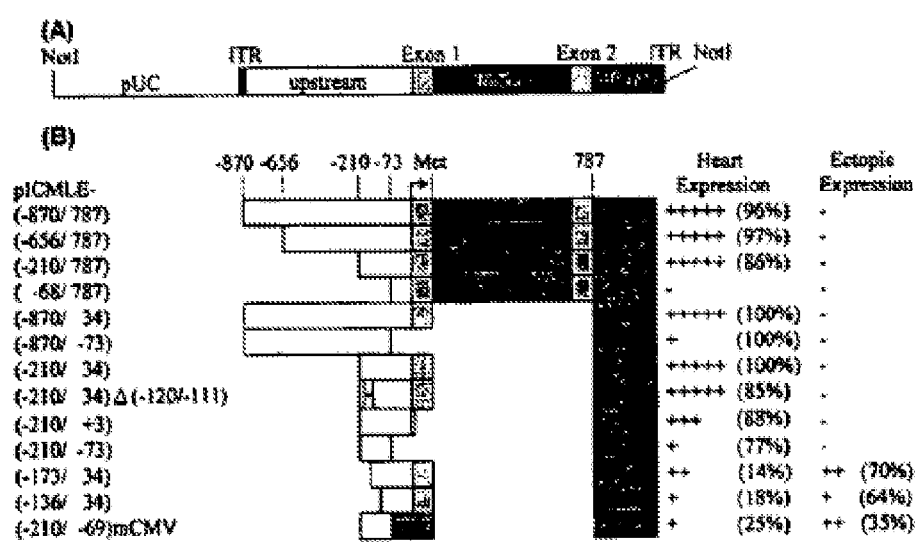
FIG. 5A shows schematic map of pICMLE.
FIG. 5B shows locations and expression levels of GFP in 3 days.

To determine the regulatory cis-elements in the proximal region of the zebrafish cmlc2, upstream series deletion fragments linked with GFP genes (FIG. 5) were constructed. Based on a transient assay, the GFP-positive signals that appeared in the 3-dpf embryos are summarized in FIG. 3. High levels of fluorescence were observed in the hearts of embryos injected with the fragments pICMLE-(−870/787), -(−656/787), -(−210/787), -(−870/34), and -(−210/34). These results led us to conclude that fragment −210/34 was a minimal promoter consisting of cis-regulatory elements required for heart specificity.

GFP expression was noted in the heart and nonheart tissues and cells (e.g., skin, skeletal muscles, eyes, blood cells, spinal cords, and yolk sacs) of embryos injected with either the pICMLE-(−173/34) or -(−136/34) fragments. The ectopic expression of GFP was not noted in embryos injected with either the pICMLE-(−210/34) or -(−870/34) fragments. We propose that fragment −210/−173 may play an important role in restricting the ectopic (nonheart) expression of cmlc2.

It was found that the −72/34 sequence within the −210/34 segment was essential for expressing GFP in the heart; the level of fluorescence in hearts declined fivefold in the embryos injected with pICMLE-(210/34) versus those injected with -(−210/−73). The latter construct did not contain −72/34 sequences. The tendency of the decline in fluorescence was also observed in embryos injected with pICMLE-(−870/−73) vs. those injected with -(−870/34). The −72/34 sequence was also missing in the construct of pICMLE-(−870/−73). It was noted that the level of fluorescence in the hearts decreased 1.7-fold in the embryos injected with pICMLE-(−210/34) vs. those injected with -(−210/3). The latter construct did not include 4/34 sequences, which contained the 5' untranslated region of the zebrafish cmlc2. Thus, the expression level of transgenic GFP in embryos decreased significantly when embryos were injected with a construct lacking the transcriptional start site and 5' untranslated region of cmlc2. These findings suggest that there are regulatory elements within the 5' untranslated region.

When a linearized plasmid pICMLE-(−210/34)Δ(−120/−111), in which G at −119 combined with TATTTA at −118/−113 was deleted from fragment −210/34, the GFP was still specifically and highly expressed in the hearts of transgenic embryos. Moreover, there was not a typical TATA consensus box near the transcription start site of the zebrafish cmlc2. As concluded, the zebrafish cmlc2 that was cloned in this application is a TATA-less promoter and that G at −119 combined with neighboring A/T-rich sequences is not a sole element for controlling heart-specific expression.

Although its intensity was relatively faint, the GFP expression in all the embryos injected with fragment pICMLE-(−210/−73) was exclusively seen in hearts. In addition, embryos with a −210/−69 sequence fused with the CMV minimal promoter were injected. Results showed that GFP was expressed in the heart as well as in other tissues. Therefore, the −210/−73 sequence acted as a basal element, allowing the exogenous GPF gene to be expressed in the heart, but this element was not capable of repressing the nonspecific expression driven by the CMV promoter.

The high-level, heart-specific expression of GFP in embryos injected with fragments pICMLE-(−870/787), -(−656/787), and -(−210/787) were similar to those observed in embryos injected with the fragments pICMLE-(−870/34) and -(−210/34), which were missing from the intron 1 of cmlc2. Thus, the intron 1 of the zebrafish cmlc2 was not involved in heart-specific regulation.

Compared with embryos injected with the fragment pICMLE-(−210/34) containing AAV-ITR, the level of fluorescence in hearts was remarkably reduced, 2.5-fold, in embryos injected with the fragment pCMLE-(−210/34) that did not contain AAV-ITR. No differences were noted between these two types of embryos in terms of exogenous GFP-signal tissue distribution. These results were consistent with those of embryos injected with the fragment pICMLE-(−210/−73) with or without AAV-ITR. The green fluorescent level was relatively low (++) in the hearts of embryos injected with pICMLE-(−210/−73) due to the absence of the −72/34 sequence; in comparison, no signal was detected in the hearts of embryos injected with pCMLE-(−210/−73), that is, not flanked by AAV-ITR.

1.16 Injection of Morpholino Antisense Oligonucleotides

Several transcription factors are predicted for binding the cis-elements located in the upstream region of zebrafish cmlc2. To determine whether Nkx2.5 and GATA-4 are specifically involved in gene regulation of the zebrafish cmlc2, we injected nkx2.5- and gata-4-MO into the embryos of the cmlc2::GFP transgenic line. In control groups, EGFP-MO was injected. The intensity of GFP decreased remarkably (at concentrations of 2.3 and 4.6 ng) or that GFP disappeared (at concentrations of 9.2 and 11.5 ng). In addition, cTnT-MO was also injected. Results showed that the heart stopped beating, the epicardium became enlarged, and blood circulation ceased. The phenotype of morphant was exactly the same as the silent heart mutant $sih^{tc300b}$, which was described by Sehnert et al. (*Nat Genet* 31: 106-110). Only a few embryos in the highest concentration (11.5 ng) groups showed heart enlargement. Like the nkx2.5-MO or gata-4-MO injection groups, the phenotype of morphant did not change in the embryos injected with the nkx2.5-MO and gata-4-MO combination.

1.17 Transgenic Line With GFP-Expression in All Muscles Resulting From Injection of the Fragment Containing a Single Nucleotide Substitution After screening and sequencing of the PCR products, we arbitrarily selected a pICMLE9-mutated (−870/787) clone showing three substitutions between nucleotide positions −870 and 787: G replaced by A at −701 (G/−701/A), G/−119/A, and C/598/T. When this GFP-fused mutated fragment was microinjected into zebrafish embryos, GFP was expressed not only in the heart, but also in the skeletal and smooth muscles of transgenic embryos. Results from a transient assay performed using various deletions of the mutated fragment showed that fragment pICMLE-(−210/34) containing a G/−119/A was sufficient to generate embryos with the expected GFP expression in the heart, plus ectopic expression in the skeletal and smooth muscles. Furthermore, a germ-line transmitted transgenic zebrafish possessing GFP in the all three muscle types was also generated by injecting fragment pICMLE-(−870/787) containing the mutated sequences. Expression of GFP was observable in the heart after 16.5-hpf, whereas signals were seen in the skeletal and smooth muscles (blood vessel and intestine) after 21-hpf. This unique expression pattern, due to introducing the mutated gene construct, was stably transmitted.

Acknowledged prior arts showed that the identity of cmlc2 promoter between zebrafish and rat is considerably low. In addition, the promoter alignments between zebrafish and rat revealed that the relevant conserved regions (i.e. HF-1, HF-2 and HF-3; of cmlc2 promoter, as presented in rats and chicks, are absent in zebrafish. Furthermore, zebrafish cmlc2 is TATA-less gene whereas rat cmlc2 is not.

Example 2

Procedure of this example was similar to that of Example 1. The major difference between Example 2 and Example 1 was that the gene segment encoding GFP in the plasmid construct, pICMLE, was replaced with that encoding red fluorescent protein (RFP, CLONETECH). The plasmid construct containing the gene encoding RFP had 5937 bp and was designated as pICMLR.

Figure 6:
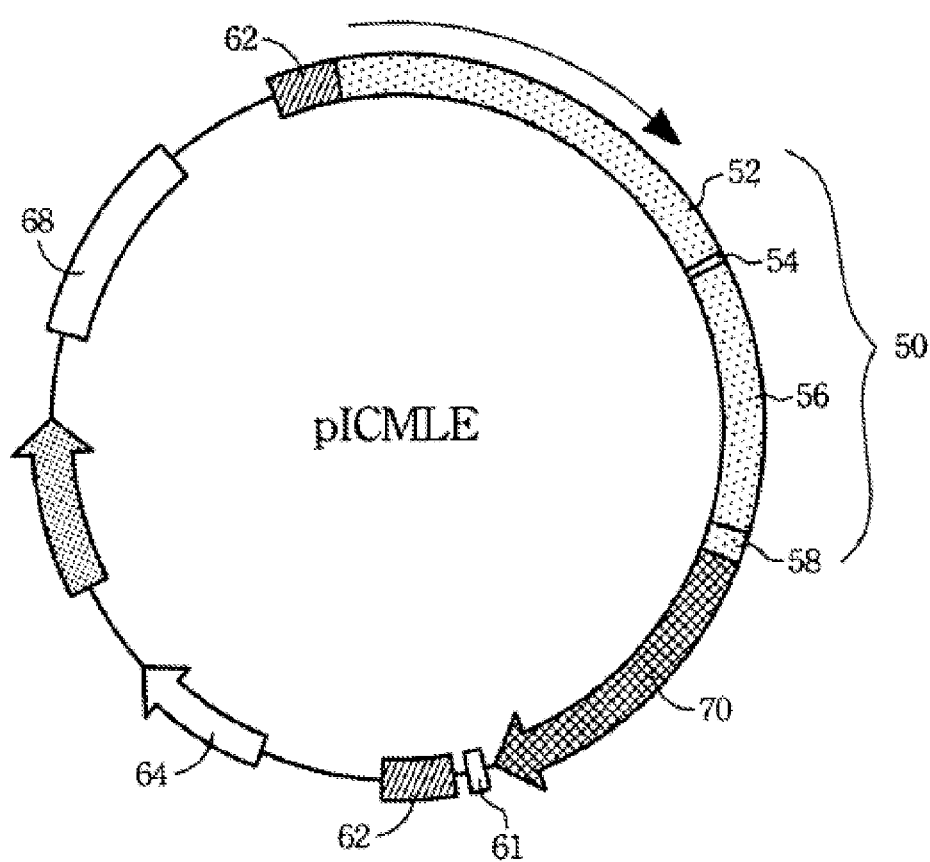
FIG. 6 is a structural view of a plasmid construct, pIC-MLE, illustrating the composition of the construct in accordance with the present invention.

Referring to FIG. 6, the nucleotide sequence of the cmlc2 gene 50 includes a 870-bp segment of the 5' upstream regulatory region 52 (454-1323), a 39-bp segment of the exon 1 54 (1324-1362), a 682-bp segment of the intron 1 56 (1363-2044) and a 69-bp segment of the exon 2 58 (2045-2110). This 1.6-kb segment (FIG. 2) was then fused with RFP cDNA 70 (CLONETECH) to form a cassette. The cassette was flanked on its both sides by 145-bp inverted terminal repeats 62 (260-1323 and 3128-3264, respectively) which are derived from an adeno-associated virus (AAV-ITR). Between the inverted terminal repeat 62 (3128) and the stop codon of the RFP cDNA 70 (2830) included a fragment containing SV40 poly-A signal sequence 61 (2931-2983). As shown in FIG. 6, the pICMLR further comprised f1 single-strand DNA origin 64 (3499-3953), ampicillin resistance gene 66 (start codon 4085-4087; stop codon 4943-4945) and Col Elorigin of replication 68 (5093-5736).

FIG. 8 showed results of microinjecting the DNA sample into embryos of zebrafish. Among 86 injected embryos, 69 embryos were survived (85%). 29 of these 69 survival embryos (42%) express RFP. 22 of the 29 RFP-expressed embryos (76%) were labeled with heart-specific fluorescence.

Example 3

Procedure of this example was similar to that of Example 1. The major difference is that DNA sample described in Example 1, section 1.08, was microinjected into embryos of medaka. That is, the DNA segment was randomly inserted into genome in transparent embryos of medaka.

FIG. 7 showed results of microinjecting the DNA sample into embryos of medaka. Among 86 injected embryos, 51 embryos (60%) were survived at 2 dpf. 25 (50%) of these 51 survival embryos were labeled with heart-specific fluorescence.

Example 4

Procedure of this example was similar to that of Example 1. The major differences between Example 4 and Example 1 were that the plasmid construct described in Example 2, i.e. pICMLR, was microinjected into embryos of medaka. The DNA segment was randomly inserted into genome in transparent embryos of medaka.

FIG. 9 showed results of microinjecting the DNA sample into embryos of medaka. Among 127 injected embryos, 114 embryos were survived (90%). 50 of these 114 survival embryos (44%) express RFP. 37 of the 50 RFP-expressed embryos (74%) were labeled with heart-specific fluorescence.

Acknowledged prior arts taught that the cmlc2 promoters of mice include two types. One of both was artery-type (MLC-2a), and the other was vein-type (MLC-2v). As to the promoters of fish developing from transparent embryos, such as zebrafish and medaka, it was surprisingly found that the cmlc2 promoters of the fish are more primitive types. In other words, when the plasmid construct containing the gene fragment encoding the fluorescent protein was introduced into genome of the fish, the exogenous DNA fragment was regulated by cis-regulatory elements and trans-acting factors (transcription factors) of cmlc2 promoter of the fish, thereby driving the expression of the gene product specifically in the heart.

While the preferred embodiment of the invention has been illustrated and described, it is appreciated that various changes can be made therein without departing from the spirit and scope of the invention.

What is claimed:

1. A method of producing an oviparous fish with fluorescence specifically expressed only in the heart with no expression in other tissues, the method comprising:
   (a) constructing a plasmid including a first ITR, a regulatory region, a gene encoding a fluorescent protein, an SV40 poly A and a second ITR, in order from upstream to downstream, wherein the regulatory region is operably linked to the gene encoding a fluorescent protein and is that set forth in SEQ ID NO: 8
   (b) linearizing the plasmid construct;
   (c) microinjecting the linearized plasmid construct into a fertilized egg of the oviparous fish;
   (d) incubating the microinjected egg to form an embryo;
   (e) selecting an incubated embryo that exhibits fluorescence; and
   (f) cultivating the selected embryo to maturity to produce the fish having fluorescence specifically expressed in the heart, with no expression in other tissues.

2. The method of claim 1 wherein the fish is a zebrafsh.

3. The method of claim 1 wherein the fish is a medaka.

4. The method of claim 1 wherein the protein is green fluorescent protein.

5. The method of claim 1 wherein the protein is red fluorescent protein.

6. An oviparous fish having fluorescence specifically expressed in the heart, which is produced according to the method of claim 1.

7. The oviparous fish of claim 6, which is a zebrafsh.

8. The oviparous fish of claim 6, which is a medaka.

9. The oviparous fish of claim 6, wherein the fluorescence is green.

10. The oviparous fish of claim 6, wherein the fluorescence is red.

11. A gene fragment comprising a first ITR, a regulatory region, a gene encoding a fluorescent protein, an SV40 poly A and a second ITR, in order from upstream to downstream, wherein the regulatory region is operably linked to the gene encoding a fluorescent protein and is that set forth in SEQ ID NO: 8.

* * * * *